United States Patent
Hoggarth et al.

(10) Patent No.: US 12,303,355 B2
(45) Date of Patent: May 20, 2025

(54) WOUND DRESSING

(71) Applicant: Medtrade Products Limited, Crewe (GB)

(72) Inventors: Andrew Hoggarth, Crewe (GB); Craig Hardy, Cardigan (GB); Ander Bugedo Albizuri, Cheshire (GB)

(73) Assignee: MEDTRADE PRODUCTS LIMITED, Cheshire (GB)

( * ) Notice: Subject to any disclaimer, the term of this patent is extended or adjusted under 35 U.S.C. 154(b) by 278 days.

(21) Appl. No.: 15/502,765

(22) PCT Filed: Aug. 7, 2015

(86) PCT No.: PCT/GB2015/052300
§ 371 (c)(1),
(2) Date: Feb. 8, 2017

(87) PCT Pub. No.: WO2016/020704
PCT Pub. Date: Feb. 11, 2016

(65) Prior Publication Data
US 2017/0239095 A1    Aug. 24, 2017

(30) Foreign Application Priority Data
Aug. 8, 2014 (GB) .................................. 1414146

(51) Int. Cl.
*A61F 13/00* (2024.01)
*A61F 13/01* (2024.01)
(Continued)

(52) U.S. Cl.
CPC .. *A61F 13/00063* (2013.01); *A61F 13/01017* (2024.01); *A61F 13/01034* (2024.01);
(Continued)

(58) Field of Classification Search
CPC .......... A61F 13/00063; A61F 13/00017; A61F 13/00034; A61F 13/00038; A61F 13/0206;
(Continued)

(56) References Cited

U.S. PATENT DOCUMENTS 5,836,970 A * 11/1998 Pandit .................... A61L 15/225
606/213
5,914,125 A *  6/1999 Andrews ................. A61L 15/28
424/443
(Continued)

FOREIGN PATENT DOCUMENTS

EP      1 923 077 A1    5/2008
GB      2290031 A  * 12/1995 ............. B32B 27/08
(Continued)

OTHER PUBLICATIONS

International Search Report and Written Opinion for corresponding PCT Application No. PCT/GB2015/052300.

*Primary Examiner* — Jessica Arble
(74) *Attorney, Agent, or Firm* — Tarolli, Sundheim, Covell & Tummino LLP

(57) ABSTRACT

The present invention relates to wound dressings. In particular, the invention relates to antimicrobial wound dressings, methods of making the same and uses of the same. The wound dressing of the present invention comprises a wound contact layer and an absorption layer, wherein the wound contact layer comprises at least one antimicrobial agent and wherein the lateral wicking rate of the wound contact layer is the same or higher than the lateral wicking rate of the absorption layer. The wound dressing of the present invention provides an absorbent, conformable and anti-microbial medical device that may be used in a variety of medical situations, including post and/or pre-operative.

18 Claims, 3 Drawing Sheets

(51) Int. Cl.
*A61F 13/02* (2006.01)
*A61F 13/0203* (2024.01)
*A61F 13/0206* (2024.01)
*A61L 15/26* (2006.01)
*A61L 15/42* (2006.01)
*A61L 15/44* (2006.01)
*A61L 15/46* (2006.01)
*A61L 15/58* (2006.01)
*A61L 15/60* (2006.01)

(52) U.S. Cl.
CPC .... *A61F 13/01038* (2024.01); *A61F 13/0206* (2013.01); *A61F 13/0209* (2013.01); *A61F 13/0223* (2013.01); *A61F 13/0266* (2013.01); *A61F 13/0289* (2013.01); *A61L 15/26* (2013.01); *A61L 15/425* (2013.01); *A61L 15/44* (2013.01); *A61L 15/46* (2013.01); *A61L 15/58* (2013.01); *A61L 15/60* (2013.01); *A61L 2300/206* (2013.01); *A61L 2300/404* (2013.01)

(58) Field of Classification Search
CPC ............. A61F 13/0209; A61F 13/0223; A61F 13/0266; A61F 13/0289
See application file for complete search history.

(56) References Cited

U.S. PATENT DOCUMENTS

| | | | |
|---|---|---|---|
| 6,509,388 B1 * | 1/2003 | Addison | ............... A61L 15/225 521/137 |
| 6,986,825 B1 * | 1/2006 | Squires | ............... B32B 37/0076 156/290 |
| 2004/0004014 A1 * | 1/2004 | Grossman | ............. A61F 15/002 206/440 |
| 2005/0182347 A1 * | 8/2005 | Bishop | .................. A61F 13/022 602/43 |
| 2009/0092819 A1 * | 4/2009 | Malik | ....................... B32B 7/12 428/305.5 |
| 2010/0055437 A1 * | 3/2010 | Fink | ........................ A01N 59/16 428/221 |
| 2010/0198127 A1 * | 8/2010 | Addison | ........... A61F 13/00995 602/48 |
| 2010/0204667 A1 * | 8/2010 | Chakravarthy | ..... A61F 13/0279 604/369 |
| 2011/0184080 A1 * | 7/2011 | Schonberger | ........... A61L 15/26 521/90 |
| 2012/0215193 A1 * | 8/2012 | Siniaguine | ........ A61F 13/00029 604/378 |
| 2013/0131621 A1 | 5/2013 | Van Holten et al. | |
| 2014/0228786 A1 * | 8/2014 | Croizat | ................... A61F 13/53 604/319 |
| 2015/0320434 A1 * | 11/2015 | Ingram | ................... A61M 1/90 606/131 |

FOREIGN PATENT DOCUMENTS

| | | | | |
|---|---|---|---|---|
| WO | 2005/065604 A1 | 7/2005 | | |
| WO | 2007/030601 A2 | 3/2007 | | |
| WO | WO-2007046806 A1 * | 4/2007 | ............. | A61L 15/18 |

* cited by examiner

WOUND DRESSING

RELATED APPLICATIONS

The present application is a U.S. National Stage under 35 USC 371 patent application, claiming priority to Serial No. PCT/GB2015/052300, filed on Aug. 7, 2015; which claims priority to GB 1414146.9, filed Aug. 8, 2014, the entirety of both of which are incorporated herein by reference.

TECHNICAL FIELD

The present invention relates to wound dressings. In particular, the invention relates to antimicrobial wound dressings, methods of making the same and uses of the same.

BACKGROUND

Topical wound dressings for use in the treatment of wounds or other openings at a physiological target site on a human or animal body which are exuding blood and/or other bodily fluids have been known for some time. The materials used to make the wound dressings act to absorb the blood and/or other bodily fluids, and also stem the flow of such fluids from the body. Materials for wound dressings are described in, for example, WO2010031995 to MedTrade Products Limited, and are commercially available.

The management of exudate is of course essential and critical during wound care and surgical procedures. The aim of managing the exudate is essentially to provide a moist wound environment at the wound bed to minimise the risk of maceration, which in turn may reduce the negative impact upon the human or animal body and also shorten the length of time the patient will take to recover.

Another important consideration, and a focus of the present invention, is the management of microorganisms such as bacteria at the wound site to reduce and prevent the risk of infection. Without suitable treatment or preventative measures, bacteria on the skin and at the wound site can repopulate and migrate into the bloodstream, placing a patient at risk of infection.

Wound dressings containing antimicrobial agents are known. Such wound dressings can comprise fibres and polymers and be in the form of textiles, gels, etc. The dressings can contain an antimicrobial agent within a layer of absorbent material, whilst some have been known to include an antimicrobial agent in an outermost layer.

A problem arises in incorporating an antimicrobial agent into a wound dressing in a sufficiently high concentration for it to be effective.

Biopatch® is a wound dressing, generally used for securing catheters, for delivering an antimicrobial agent at the site of insertion of the catheter into the body. The dressing contains chlorhexidine gluconate (CHG) bonded to collagen within the dressing. However, such a wound dressing requires the presence of a collagen cross-linked biopolymer which has an affinity to the antimicrobial agent enabling the antimicrobial agent to reversibly bind thereto. A collagen cross-linked biopolymer delivers a controlled release of antimicrobial agent over time. However, this is not desirable in cases when it is necessary to deliver a large quantity of antimicrobial agent faster with the aim of killing microorganism quicker.

A further consideration when treating wounds, it that it is desirable for a wound dressing to absorb wound exudate and transfer it away from the wound site whilst also maintaining a moist environment to promote healing of the wound. When managing microorganisms, it is important that as much of the wound exudate as possible is exposed to the antimicrobial agent and at as early a stage as possible.

There is therefore a need to develop improved methods of incorporating antimicrobial agents into wound dressings to prevent the repopulation and migration of microorganisms such as bacteria at the wound site and into the bloodstream.

SUMMARY

The present invention has been made from a consideration of the aforementioned limitations and problems.

According to a first aspect of the present invention, there is provided a wound dressing comprising a wound contact layer and an absorption layer, wherein the wound contact layer comprises at least one antimicrobial agent and wherein the lateral wicking rate of the wound contact layer is the same or higher than the lateral wicking rate of the absorption layer.

The wound dressing of the present invention is capable of absorbing and rapidly spreading wound exudate from the wound site in the wound contact layer. The wound contact layer comprises an antimicrobial agent. The wound exudate that is rapidly spread in the wound contact layer is exposed to a greater amount of the antimicrobial agent before it passes through to the absorption layer. Beneficially, this reduces the level of microorganisms in the wound exudate. It also means that the antimicrobial agent is exposed to both the wound site and the surrounding healthy tissue, which significantly reduces the risk of infection.

Moreover, the absorption layer enables the transmission of wound exudate away from the wound site, which allows the wound site to remain moist whilst not being too wet. Beneficially, this promotes healing and minimises the risk of maceration.

The wound dressing of the present invention provides an absorbent, conformable and anti-microbial medical device that may be used in a variety of medical situations, including post and/or pre-operative.

The wound dressing is absorbent and can be used to absorb exudate and minimise wound site infection by covering the peri-wound area of a wound caused by vascular and non-vascular percutaneous medical devices such as IV catheters, central venous lines, arterial catheters, dialysis catheters, mid-line catheters, drains, chest tubes, externally placed orthopaedic pins and epidural catheters.

The wound dressing may also be used for the management of infected chronic wounds and those wounds at risk of infection.

The terms 'proximal' and 'distal' are used relative to a wound site. For example, the term 'proximal' is used herein to refer to a surface of a layer that faces toward the wound site and the term 'distal' is used herein to refer to a surface of a layer that faces away from the wound site.

The wound contact layer is intended for direct contact with the wound. The wound contact layer may have a surface proximal to the wound site that contacts the wound and a surface distal to the wound site that is attached to the absorption layer. In use, the face of the proximal surface will be applied directly to the wound site and surrounding tissue.

The wound contact layer is operable to transmit wound exudate from the wound site to the absorption layer. It is desirable that the wound contact layer has a high lateral wicking rate to enable the wound exudate to absorb and rapidly disperse laterally through the layer and then rapidly pass into the absorption layer. It is also desirable for the wound contact layer to have a lower absorbency than the absorption layer to facilitate the passage of the wound exudate through to the absorption layer.

A high lateral wicking rate refers to the rapid speed at which the wound contact layer will absorb wound exudate and allow it to disperse throughout the layer. Typically, the lateral wicking rate of the wound contact layer will be from 0.1-20 seconds, preferably from 0.5-10 seconds and more preferably from 1-5 seconds as measured by the test method described herein. Rapidly dispersing the wound exudate in the wound contact layer activates more of the antimicrobial agent in that layer. This has the beneficial effect of improving antimicrobial activity at the wound interface and throughout the dressing.

The lateral wicking rate is preferably uniform across the wound contact layer. A uniform lateral wicking rate provides a more even distribution of wound exudate throughout the wound contact layer.

The wound contact layer may have an absorbency of less than the absorbency of the absorption layer. Absorbency is typically measured as grams of fluid that can be absorbed per gram of absorbent. The absorbency of the wound contact layer may be less than 20 g/g, preferably less than 15 g/g and most preferably less than 10 g/g. The absorbency is based on the test methods described herein.

The wound contact layer may comprise a biologically acceptable polymer material that has a wicking rate the same or equal to that of the absorption layer. Suitable biologically acceptable polymer materials may be selected from the group consisting of polyurethane, polyvinyl chloride, Styrofoam, polyimide and silicone.

Preferably, the biologically acceptable polymer is polyurethane.

The wound contact layer may be in the form of a textile, a film or a foam. Preferably, the wound contact layer is in the form of a foam, preferably still an open-celled foam. Thus, the biologically acceptable polymer materials may be selected from the group consisting of polyurethane foam, polyvinyl chloride foam, Styrofoam, polyimide foam and silicone foam.

Good results have been observed wherein the wound contact layer comprises polyurethane foam. The polyurethane foam is open-celled so as to allow for the passage of wound exudate through the foam and into the absorption layer. Closed-celled foams are not appropriate for the wound contact layer as they do not allow the passage of fluid through the foam.

The wound contact layer may have a thickness of from 0.5-4 mm, preferably 1-3 mm and more preferably 1.5-2 mm. Good results have been observed with a wound contact layer having a thickness of around 3 mm.

The wound contact layer may have any suitable shape common in the field of wound dressings. Typically, the wound contact layer will have a rectangular, elliptical or circular shape.

The wound contact layer may have a surface area the same as or less than that of the absorption layer.

It is a problem with existing wound dressings that wound contact layers are prone to distort when wet with wound exudate. This is particularly evident in examples of wound dressings that do not comprise a wound contact layer such that an absorption layer contacts the wound directly. The distortion of the wound dressing typically occurs when the wound contact layer swells and expands outwardly. The effect is a curling of the wound contact layer away from the skin. This is undesirable as sections of the wound dressing lift off the skin, thereby reducing the strength of the contact between the skin and the wound dressing. Such a curling of the wound dressing can also leave it vulnerable to being caught and tearing off during routine activity, such as patient movement or treatment. This can lead to discomfort and, in some instances, the need to replace the dressing. It is therefore highly desirable to provide a wound dressing that avoids and alleviates this problem.

It has been discovered that compressing the wound contact layer to a width less than its original width and/or having a wound contact layer with a density of greater than 0.06 g/cm$^3$ provides a wound contact layer that reduces or removes distortion when wet with wound exudate. The wound contact layer does not curl and lift off the skin nor lose its shape when swelled and wet with wound exudate. The wound contact layer does not expand outwardly but can expand vertically.

Thus, the wound contact layer may be compressed and/or the wound contact layer may have a density of greater than 0.06 g/cm$^3$.

The wound contact layer may have a density of greater than 0.06 g/cm$^3$.

The wound contact layer may be compressed to the desired density or alternatively the wound contact layer may be manufactured to the desired density using standard manufacturing techniques for the materials forming such a layer.

In some embodiments, the wound contact layer may have a density of greater than 0.10 g/cm$^3$, preferably greater than 0.15 g/cm$^3$ and more preferably greater than 0.2 g/cm$^3$. In some embodiments, the wound contact layer may have a density of greater than 0.3 g/cm$^3$. Thus, densities of greater than 0.07, 0.08, 0.09, 0.10, 0.11, 0.12, 0.13, 0.14, 0.15, 0.16, 0.17, 0.18, 0.19, 0.20, 0.21, 0.22, 0.23, 0.24, 0.25, 0.26, 0.27, 0.28, 0.29, 0.30, 0.31, 0.32, 0.33, 0.34, 0.35, 0.36, 0.37, 0.38, 0.39, 0.40 are envisaged.

The wound contact layer may be compressed to a width less than that of its original width.

Compressing the wound contact layer increases its density whilst still allowing for the flow of wound exudate therethrough. However, if the wound contact layer is compressed too much, it will be too dense for wound exudate to flow therethrough.

The wound contact layer may be compressed to a width of from 20-90% of its original width, more preferably from 30-60% of its original width and most preferably from 40-55% of its original width. Good results have been observed where the wound contact layer has been compressed to a width of around 50% of its original width. For example, the wound contact layer may comprise an open celled polyurethane foam having an original width of 3 mm, compressed to a thickness of 1.5 mm.

It has also been discovered that uncompressed foams, whilst being feasible in the wound dressings of the present invention, can lead to disadvantages such as healthy wound tissue migrating into the foam. This can lead to trauma and discomfort on removal of the dressing.

The wound contact layer may be dimensionally stable. The term dimensionally stable is used herein to refer to a material that does not expand beyond 10% of its original dimension when wet.

The wound contact layer comprises at least one antimicrobial agent.

Antimicrobial agents are used primarily to kill microorganisms or inhibit their growth. It is important in wound management to remove or reduce the risk of infection at the wound site or in the bloodstream. In the wound dressings of the present invention, the antimicrobial agent is operable to kill or inhibit the growth of microorganisms at and around the wound site and in the wound exudate.

The antimicrobial agent may act as an antibacterial, an antifungal, or both. Preferably, the antimicrobial agent is antibacterial.

The wound contact layer may comprise one or more antimicrobial agents. For example, the wound contact layer may comprise two, three, four or five different antimicrobial agents.

Antimicrobial agents for use in wound dressings will be familiar to a person skilled in the art. Suitable antimicrobial agents for use in the wound dressings of the present invention may be selected from the group consisting of silver, polyhexamethylene biguanide (PHMB), chlorhexidine gluconate (CHG), chitosan, chitosan derivatives, octenidine, iodine and combinations of any two or more thereof. Preferably, the antimicrobial agent is selected from CHG, silver of a combination thereof. More preferably, the antimicrobial agent is CHG, since CHG has a broader activity range than other antimicrobials.

The CHG is preferably applied in the form of a solution. The solution comprises CHG in water. The solution is preferably British Pharmacopoeia (BP) grade. Preferably, the CHG solution is a 20% CHG solution. Other concentrations are suitable for use in the present invention. However, the more concentrated the solution, the thicker it is. This affects the absorption of the solution. Also, the more dilute the concentration is, the more liquid has to be applied. As such, increased drying is required.

The antimicrobial agent is typically applied to the wound contact layer in the form of a solution. If the antimicrobial agent is in solid form, such as a powder or particulate form, it may be mixed with a solution prior to application to the wound contact layer. Preferably, the antimicrobial agent dissolves in the fluid.

The antimicrobial agent in solution may be applied to the wound contact layer by any liquid application process known in the art. Such methods may include spraying the solution onto a surface of the wound contact layer, pipetting the solution onto a surface of wound contact layer, dip coating the wound contact layer in the solution, and the like.

Prior to application, the wound dressing is preferably dry. It is therefore desirable to dry the wound contact layer following application of the antimicrobial agent. The drying process can comprise driving off any excess fluid from the wound contact layer after the solution containing the antimicrobial agent has been applied. This is typically performed by heat treating the wound contact layer. Suitable heat treatment techniques will be familiar to a person skilled in the art. They may include treatment in an oven or infrared treatment.

In some embodiments, the wound contact layer and the absorbent layer are formed into the wound dressing prior to application of the antimicrobial agent. In such embodiments, the techniques for applying the antimicrobial agent are the same as described herein.

In some embodiments, the antimicrobial agent is introduced as an additive in the process for preparing the biologically acceptable polymer.

The amount of antimicrobial agent required in the wound contact layer may vary depending on the specific antimicrobial agent, or combination of agents, applied. For example, certain antimicrobial agents, such as octenidine, may be required in a lesser amount than CHG.

The wound contact layer may comprise around 0.1-2 wt % of the antimicrobial agent. Where the antimicrobial agent is CHG, the wound contact layer may comprise from around 25-150 mg of CHG, preferably around 50-100 mg. Good results have been observed where the wound contact layer comprises around 85-95 mg CHG.

Typically, the antimicrobial agent bonds to the surface of the wound contact layer.

The antimicrobial agent may be dispersed across and/or throughout the wound contact layer. Preferably, the antimicrobial agent is dispersed uniformly across and/or throughout the wound contact layer. This improves the efficacy of the antimicrobial action as a greater proportion of the wound exudate is exposed to the antimicrobial agent. Also, more of the antimicrobial agent is released at the wound interface. It is beneficial to also deliver the antimicrobial agent to the tissue surrounding the wound to prevent bacteria or microbes entering the wound through the channel between the dressing and the skin.

As least a portion of the antimicrobial agent may migrate into the absorption layer. This can occur during application of the antimicrobial agent to the wound contact layer and/or in use when the wound exudate passes through the wound contact layer into the absorption layer. It is beneficial to have antimicrobial agent in the absorption layer, as this enables the antimicrobial agent to act on the wound exudate in a greater proportion of the dressing as well as at the wound interface. The antimicrobial agent in the wound contact layer can act on microbes, such as bacteria, at the wound interface whilst the antimicrobial agent in the absorption layer can act on microbes that have entered the wound dressing so as to kill or inhibit bacterial growth within the dressing.

Thus, the wound dressing of the present invention may comprise a wound contact layer and an absorption layer, wherein the wound contact layer and the absorption layer comprise at least one antimicrobial agent and wherein the lateral wicking rate of the wound contact layer is the same or higher than the lateral wicking rate of the absorption layer.

The concentration of antimicrobial agent is typically higher in the wound contact layer than the absorption layer.

The absorption layer is operable to absorb wound exudate that passes through the wound contact layer. The absorption layer swells as it absorbs wound exudate. Typically, the absorption layer may swell by greater than 5%, preferably greater than 10% and more preferably greater than 15% when fully saturated.

The absorption layer may have a surface proximal to the wound site that contacts the wound contact layer and a surface distal to the wound site that faces away from the wound.

The absorption layer has an equal or lower lateral wicking rate than the wound contact layer. Typically, the lateral wicking rate of the absorption layer will be from around 15-60 seconds or more as measured by the test method described herein.

It is desirable for the absorption layer to have a higher absorbency than the wound contact layer to facilitate the passage of the wound exudate through the wound dressing. The absorbency of the absorption layer may be greater than 5 g/g, preferably greater than 8 g/g and more preferably greater than 12 g/g. In some instances, the absorbency of the absorption layer may be greater than 20 g/g.

The absorption layer may comprise a biologically acceptable polymer material that has a wicking rate the same or lower than the wound contact layer. Preferably the biologically acceptable polymer material will also have an absorbency greater than that of the wound contact layer. Suitable biologically acceptable polymer materials may be selected from the group consisting of polyurethane and a superabsorbent material selected from polymeric materials such as poly(vinyl) alcohol (PVA), poly(ethylene oxide) (PEO) and poly(acrylic acid).

Preferably, the biologically acceptable polymer is polyurethane. The polyurethane of the absorption layer may have a pore size that is larger than that in the wound contact layer.

The absorption layer may be in the form of a foam.

Good results have been observed wherein the absorption layer comprises polyurethane foam. The polyurethane foam is typically open-celled.

The absorption layer typically has a greater thickness than that of the wound contact layer. The absorption layer may have a thickness of from 1-6 mm, preferably 2-5 mm and more preferably 3-4 mm. Good results have been observed with an absorption layer having a thickness of around 4 mm.

The absorption layer may have any suitable shape common in the field of wound dressings. The absorption layer may have the same shape as the wound contact layer. Preferably, the absorption layer will follow the same shape and contour as the wound contact layer.

The absorption layer may comprise a further antimicrobial agent. The further antimicrobial agent may be the same or different to the antimicrobial agent in the wound contact layer.

The further antimicrobial agent may be selected from the group consisting of silver, polyhexamethylene biguanide (PHMB), chlorhexidine gluconate (CHG), chitosan, chitosan derivatives, octenidine, iodine and combinations of any two or more thereof. Preferably, the further antimicrobial agent in the absorption layer is silver.

It is beneficial to have a further antimicrobial agent in the absorption layer as this will act on microbes that have entered the dressing and/or have passed through from the wound contact layer. Such action will inhibit the growth of microorganisms, such as bacteria, within the dressing.

The absorption and/or wound contact layers may comprise one or more additional antimicrobial agents.

A proximal surface of the absorption layer may be attached to a distal surface of the wound contact layer. The respective layers may be attached using heat bonding or at least one adhesive. Where the absorption layer and the wound contact layer are both polyurethane based, they may be physically bonded to each other by bringing the two layers together under heat and pressure.

Preferably, the absorption layer is attached to the wound contact layer using an adhesive.

The adhesive may be applied to either or both of the surfaces that will be contacted with each other. The adhesive may be applied across substantially all of either or both surfaces or, alternatively, across a portion or portions thereof.

The adhesive may be in the form of a powder, a liquid, a web or a net. The web may be an acrylic web.

The adhesive may comprise a meltable adhesive and/or a pressure sensitive adhesive, or the like. The meltable adhesive may be a heat-bonding adhesive. The pressure sensitive adhesive may be acrylic based.

The adhesive may be in the form of a layer between the absorption layer and the wound contact layer. Preferably, the layer is porous so as to allow transmission of the wound exudate from the would contact layer into the absorbent layer. If the adhesive covers the entire surface of either the absorption layer or the wound contact layer, it will not be feasible for wound exudate to pass from the wound contact layer into the absorption layer.

Preferably, the adhesive is a powder adhesive. The dry powder may be scattered onto a surface to be attached and then passed through a heat tunnel to laminate the absorption layer and wound contact layer.

The wound dressing of the present invention may further comprise a backing layer.

A proximal surface of the backing layer is typically attached to the distal surface of the absorption layer. The layers can be attached by any of the means referred to herein. Preferably, the backing layer is attached to the absorption layer using an adhesive. The adhesive is preferably an acrylic based pressure sensitive adhesive but may comprise any of the adhesives and be applied by any of the methods referred to herein.

The backing layer serves as a barrier and is operable to prevent microorganisms, such as bacteria, from entering the wound dressing from an external source, such as clothing, etc. The backing layer may also be waterproof. Further, the backing layer also serves to retain the wound exudate within the wound dressing and prevent it leaching out of the wound dressing.

The backing layer may have a surface area greater than that of the absorption layer and/or the wound contact layer. In such instances, there may be an overlap section whereby the backing layer extends beyond the edge of the absorption and wound contact layers.

The backing layer may be permeable to air and moisture but impermeable to water droplets and bacteria. In this regard, no water droplets or bacteria can penetrate the backing layer and enter the wound dressing.

The backing layer may be permeable to moisture. The backing layer may be occlusive. The permeability of the backing layer may be measured using established industry practices, such as the Paddington cup method (BS:EN 13726).

The backing layer may therefore comprise a material that is porous to air and moisture vapour but non-porous to water, such as water droplets, and microorganisms, such as bacteria.

The backing layer may be in the form of a film, a foam, or a combination thereof. Preferably, the backing layer is in the form of a film.

The backing layer may comprise any biologically acceptable polymer material that is impermeable to water droplets and microorganisms but permeable to air and moisture. Suitable biologically acceptable polymer materials for the backing layer may be selected from the group consisting of polyurethane and polyethylene.

The backing layer may comprise a polyurethane film, a polyurethane foam, a combination of the two, or a polyethylene film. The backing materials are preferably closed-celled.

Preferably, the backing layer comprises a polyurethane film.

The thickness of the film varies depending on the material of the backing layer

For example, polyurethane and polyethylene films may have a thickness of from 10-100 microns; polyurethane foam/film combinations typically have a thickness in the range 200-600 microns. A particularly preferred example of a suitable polyurethane film envisaged by the present invention is polyurethane wherein the thickness of the film is 30 microns. Other options include, for example, polyurethane having a film thickness of 15 microns.

Thus, the wound dressing of the present invention may comprise a wound contact layer, an absorption layer, and a backing layer, wherein the wound contact layer comprises at least one antimicrobial agent and wherein the lateral wicking rate of the wound contact layer is the same or higher than the lateral wicking rate of the absorption layer.

The wound dressing of the present invention may comprise additional layers as desirable and as appropriate. For example, the wound dressing may comprise a second or more absorption layers. The second absorption layer may be located adjacent the first absorption layer. The second absorption layer may be operable to absorb wound exudate passing through the first absorption layer. This may be beneficial when treating wounds exuding a high amount of fluid, such as severe bleeding. The second and subsequent absorption layers may comprise any of the features described herein in relation to the absorption layer.

The second or subsequent absorption layer may comprise or consist of a superabsorbent material.

The term 'superabsorbent material' is used herein to refer to a hydrophilic material that is water-swellable, but not water soluble, and which is capable of absorbing fluid to greater than 2000% with a fluid retention of greater than 85%. Preferably, the superabsorbent material is capable of absorbing fluid to greater than 2500% with a fluid retention of greater than 90%.

The term 'water-swellable' is used herein to refer to a material that, when contacted with water or water-containing fluid, will absorb the fluid and swell, but will not substantially dissolve in that fluid.

The term 'water soluble' is used herein to refer to a material that, when contacted with water or a water-containing fluid, will dissolve in that fluid.

The superabsorbent material may be selected from polymeric materials such as poly(vinyl) alcohol (PVA), poly(ethylene oxide) (PEO) and poly(acrylic acid).

The superabsorbent material may be chemically modified. For example, the superabsorbent material may be a polymeric material obtained by graft polymerisation of acrylic acid onto a chain of carboxymethyl cellulose.

The superabsorbent material may comprise a chemically modified material selected from starch, cellulose and polymeric materials such as poly(vinyl alcohol) (PVA), poly(ethylene oxide) (PEO), and poly(acrylic acid). The poly(acrylic acid) may be a partially neutralised, lightly cross-linked poly(acrylic acid).

The terms "cross-linking" and "cross-linked" are used herein to refer to two or more polymer chains being linked by a primary bond, such as a covalent bond.

The term "lightly cross-linked" is used herein to refer to embodiments wherein the number of cross-linking primary bonds in the superabsorbent material is less than the total number of possible cross-linking bonds.

In some embodiments, the superabsorbent material is selected from polymeric materials such as PVA, PEO, and poly(acrylic acid), preferably a partially neutralised, lightly cross-linked poly(acrylic acid).

Typically, the superabsorbent material is a partially neutralised, lightly crosslinked poly(acrylic acid).

The superabsorbent material may be in the form of fibres. Typically, the superabsorbent material is in the form of non-woven fibres. The length of the fibres can be up to 100 mm, and is typically from 20-75 mm, more typically from 32 to 51 mm.

The wound dressing of the present invention may further comprise adhesion means for adhering the wound dressing to the body of a user. The adhesion means may comprise a skin contact adhesive material.

For example, the adhesion means may comprise a skin contact adhesive material that can be applied over a portion of the outermost layer of the wound dressing and a portion of the patient's skin. The adhesive material, such as a medical grade tape, may be applied after the wound dressing is in place. Alternatively, the adhesive material may be attached to the wound dressing prior to the wound dressing being applied to the patient.

Additionally or alternatively, the adhesion means may comprise a skin contact adhesive material on the proximal surface of the wound contact layer. Preferably, such adhesive material may be fashioned to extend around some or all of a peripheral portion of the wound contact layer. Such an arrangement ensures that the skin contact adhesive material does not directly contact the wound and prevent wicking of the wound exudate through the wound dressing, i.e. it will leave a central portion of the wound contact layer exposed to the wound site. Alternatively, a perforated skin contact adhesive material may extend across the surface of the wound contact layer. The perforations are suitable to allow the passage of wound exudate through the adhesive material and into the wound contact layer.

Suitable skin contact adhesives may include, but are not limited to, acrylate, silicone, polyester or polyurethane based adhesives. They can be based on hydrogels and can be porous to moisture with a high moisture vapour transmission rate. They can be applied from water emulsions, solvents or using hot melt systems. The adhesives should have a good skin tack but give minimal skin trauma on removal. They can constitute 100% coverage of the wound contact layer, or a partial coverage thereof in the form of a pattern or mesh.

Preferably, the skin contact adhesive material is selected from the group consisting of pressure sensitive adhesives, polyurethane adhesives, silicone adhesives. Preferably, the pressure sensitive adhesive is acrylic based. The silicone adhesives may be selected from common adhesives known in the art, such as Dow Corning, Bluestar, Wacker and Nusil.

The skin contact adhesive material may comprise an adhesive, such as those referred to herein, bonded to a carrier layer. The carrier layer may be coated with the skin contact adhesive. The carrier layer may have any of the features of the backing layer described herein.

The carrier layer may constitute 100% coverage of the wound contact layer, or a partial coverage thereof in the form of a pattern or mesh. For suitable operation, the carrier layer should be perforated in order to allow the passage of wound exudate through the carrier layer and into the wound contact layer.

Good results have been observed using a perforated silicone coated polyurethane film. In such embodiments, a polyurethane film, acting as a carrier layer, may be coated with an adhesive, such as silicone adhesive, and perforated. The perforated film is then bonded to the proximal surface of the wound contact layer. The silicone coated layer may bond to the wound and surrounding healthy tissue. Preferably, the silicone adhesive has a good skin tack and gives minimal skin trauma on removal.

The wound dressing of the present invention may also comprise additional components in the wound contact layer, absorption layer(s) and backing layer. Such additional components include, but are not limited to, pharmaceutical agents; wetting agents such as surfactants; growth factors; cytokines; agents which absorb agents which delay healing such as MMP's (matrix metalloproteinases) and elastase; and/or another wound dressing component, such as calcium, vitamin K, fibrinogen, thrombin, factor VII, factor VIII, clays such as kaolin, oxidised regenerated cellulose, gelatin, or collagen, etc.

Typical levels of any of these additional components could be from about 50 ppm up to about 50% by weight of the wound dressing. More typical levels would be less than 10%, still more typically less than about 5% by weight of the wound dressing. Additional components comprising less than about 1% by weight of the wound dressing are also envisaged by the present invention.

The wound dressing of the present invention is typically sterilised prior to packaging. This enables the physician or emergency responder to use the wound dressing directly from the packaging, thus saving further time.

The sterilisation may be carried out using any of the methods conventionally known in the art, such as gamma irradiation, electron beam treatment, heat treatment, x-ray, etc., or it may alternatively be carried out by treatment using ethylene oxide.

One such use for the wound dressing of the present invention is as a wound dressing for application at the site of a catheter.

In such embodiments, the wound dressing may comprise a radial slit extending from an edge of the wound dressing to a central point thereof. The central point need not necessarily be the exact centre of the wound dressing but should preferably be near or at the centre. The slit allows the wound dressing to be applied around the catheter.

The wound dressing may further comprise a central aperture suitable for receiving a catheter therethrough.

The wound dressing may be in the shape of rectangular, elliptical or circular disc.

The wound dressing of the present invention typically does not comprise collagen and/or a cross-linked biopolymer. Further, the wound dressing of the present invention typically has the antimicrobial agent applied directly to the wound contact layer and then dried to remove excess water.

According to a further aspect of the present invention, there is provided a method of manufacturing a wound dressing, the method comprising the steps of:
(a) attaching an wound contact layer to an absorption layer using an adhesive; and
(b) applying at least one antimicrobial agent to the wound contact layer;
wherein the lateral wicking rate of the wound contact layer is the same or higher than the lateral wicking rate of the absorption layer.

The adhesive may be applied to a surface of the wound contact layer and/or the absorption layer. The adhesive may comprise a powder that is scattered onto a surface of the wound contact layer and/or absorption layer. It is important to ensure that the adhesive does not result in a continuous film providing 100% coverage of the wound contact layer and/or adhesive layer, as this will prevent passage of wound exudate through the dressing. In such instances, the adhesive may be perforated to ensure that wound exudate can pass through the dressing.

The wound contact layer and absorption layer may be laminated. The lamination may be conducted by means known in the art, such as a dry-heat lamination process using a heat tunnel.

The antimicrobial agent is preferably applied to the wound contact layer after step (a). However, in some instances the antimicrobial agent may be applied to the wound contact layer as a first step and the wound contact layer is then attached to the absorption layer using an adhesive.

The antimicrobial agent may be applied by spray coating or pipetting a solution containing antimicrobial agent onto the proximal surface of the wound contact layer. Alternatively, the wound contact layer may be dipped into a solution containing the antimicrobial agent.

The method may comprise the further step of drying the wound dressing. Such a step drives off any moisture resulting from the application of the antimicrobial agent.

The drying step may be conducted by any suitable drying means for wound dressings, such as an oven.

The method may further comprise the step of attaching a backing layer to the distal surface of the absorption layer. Preferably, the backing layer is attached to the absorption layer using an adhesive as described herein.

The method may further comprise the step of attaching an adhesion means to the wound dressing. The adhesion means may comprise any of the features described herein. The adhesion means may be attached to a distal surface of the absorption layer or, if present, the backing layer. Additionally or alternatively, the adhesion means may be attached to the proximal surface of the wound contact layer.

The method of attaching the adhesion means may first comprise the step of applying an adhesive to a carrier material. The adhesive may be applied to the carrier material by any suitable means known in the art, such as for example, spray coating, pipetting, dip-coating and the like.

The method may comprise a further step of sterilising the wound dressing. The sterilisation may comprise sterilising the individual components of the wound dressing prior to formation of the wound dressing or, additionally or alternatively, sterilisation of the prepared wound dressing.

According to a further aspect of the present invention, there is provided a wound dressing as described herein for use as a medicament.

According to a further aspect of the present invention, there is provided a wound dressing as described herein for use in killing or inhibiting the growth of microorganisms.

According to a further aspect of the present invention, there is provided a wound dressing as described herein for use in absorbing fluid discharged from a physiological target, or for use in stemming a flow of a fluid discharged from a physiological target site.

The further aspects of the present invention may incorporate any of the features described in respect of the first aspect of the present invention as desired or as appropriate.

BRIEF DESCRIPTION OF THE DRAWINGS

Embodiments of the present invention will now be further described with reference to the following non-limiting examples and accompanying figures in which.

DETAILED DESCRIPTION

Figure 1:
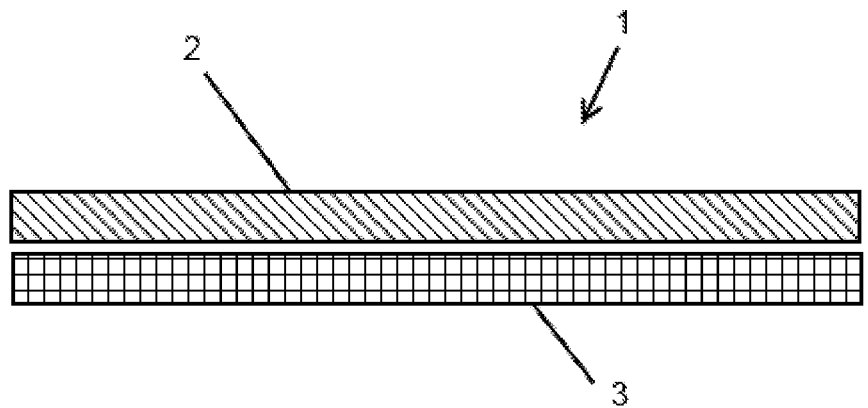
FIG. 1: is a representation of a wound dressing of the present invention.

Referring to FIG. 1, there is shown a wound dressing (1) comprising a wound contact layer (2) and an absorption layer (3). The wound contact layer comprises an antimicrobial agent (not shown).

Typically, the wound contact layer (2) is a polyurethane open celled foam having a thickness of around 3 mm. The polyurethane foam can be compressed down to a thickness of 1.5 mm and/or can have a density of greater than 0.06 g/cm³. The absorption layer (3) is typically a polyurethane foam having a thickness of around 4 mm.

A distal surface of the wound contact layer (2) and a proximal surface of the absorption layer (3) are bonded to each other using an adhesive (not shown).

Figure 2:
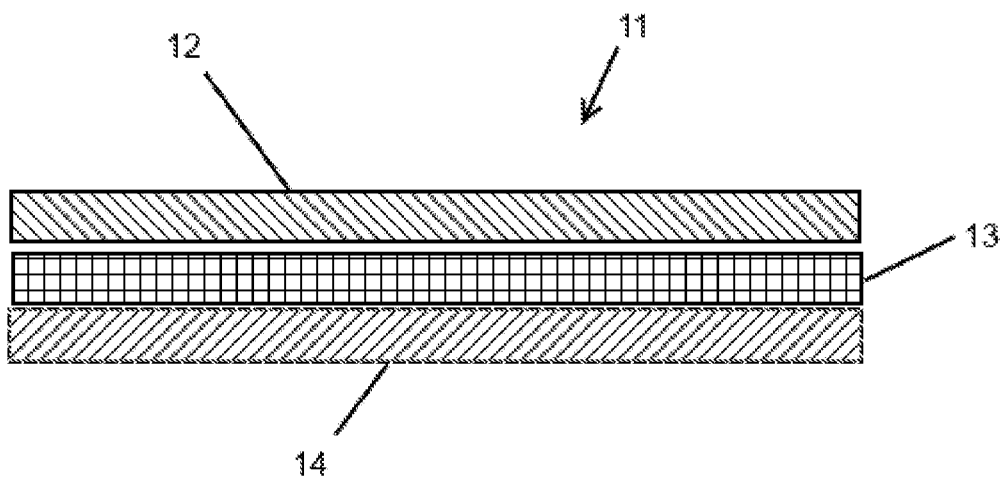
FIG. 2: is a representation of an embodiment of a wound dressing of the present invention.

Referring to FIG. 2, there is shown a wound dressing (11) comprising a wound contact layer (12), an absorption layer (13) and a backing layer (14). The wound contact layer (12) and absorption layer (13) may be the same as those shown to in FIG. 1.

The backing layer (14) typically comprises a polyurethane film. The polyurethane film typically has a thickness of around 30 microns. The backing layer (14) is permeable to air and moisture vapour but is impermeable to microorganisms, such as bacteria, and liquid droplets, such as water. A distal surface of the absorption layer (13) and a proximal surface of the backing layer (14) are bonded to each other using an adhesive (not shown).

Figure 3:
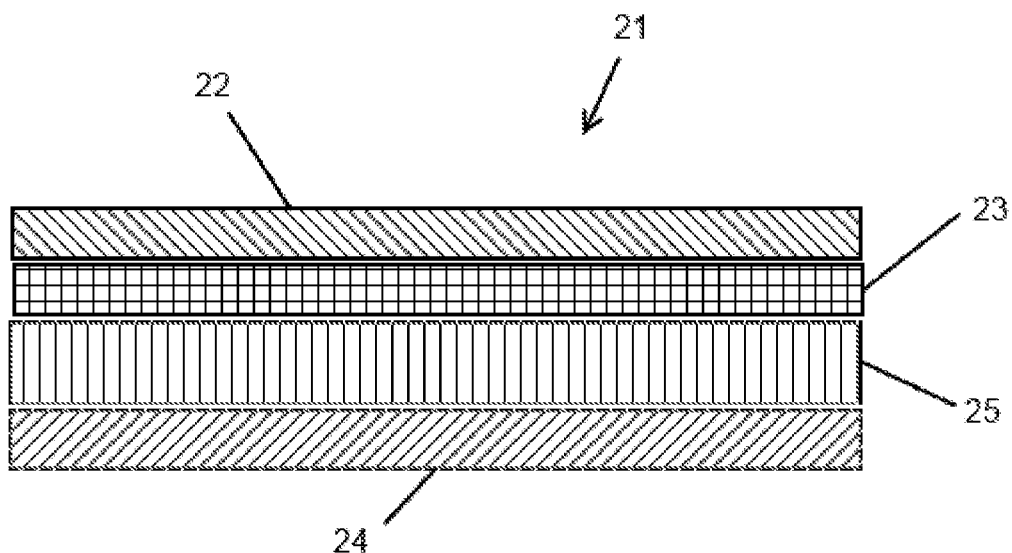
FIG. 3: is a representation of an embodiment of a wound dressing of the present invention.

Referring to FIG. 3, there is shown a wound dressing (21) comprising a wound contact layer (22), an absorption layer (23), a backing layer (24) and a superabsorbent layer (25). The wound contact layer (22), absorption layer (23) and backing layer (24) may be the same as those described in FIG. 2.

The superabsorbent layer (25) typically comprises non-woven fibrous material. The superabsorbent layer (25) is bonded to the absorption layer (23) and the backing layer (24) using an adhesive (not shown). The adhesive may be a heat bonded net.

Figure 4:
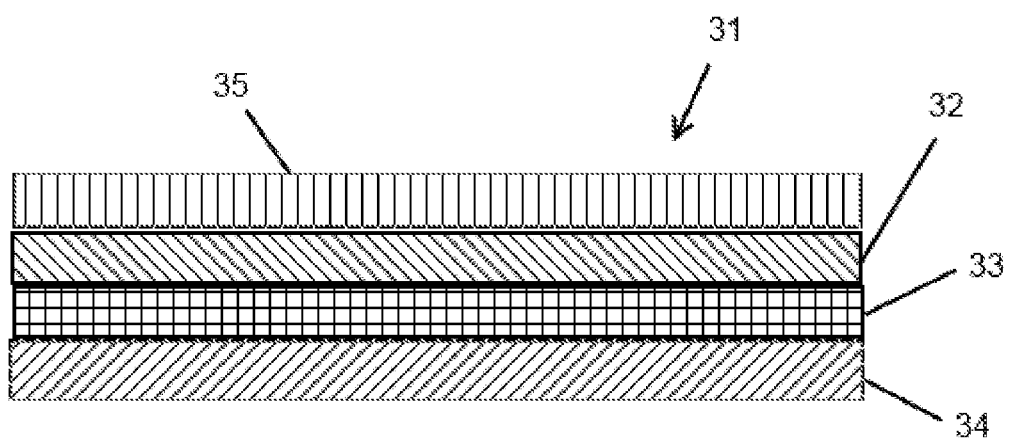
FIG. 4: is a representation of an embodiment of a wound dressing of the present invention.

Referring to FIG. 4, there is shown a wound dressing (31) comprising a wound contact layer (32), an absorption layer (33), a backing layer (34) and a skin contact adhesive layer (35). The wound contact layer (32), absorption layer (33) and backing layer (34) may be the same as those described in FIG. 2.

The skin contact adhesive layer (35) comprises a polyurethane film coated with a silicone adhesive. The film is perforated to as to allow for the passage of wound exudate into the wound contact layer (32).

The skin contact adhesive layer (35) is bonded to a proximal surface of the wound contact layer (32).

Table 1 shows changing density values for a 5 mm thick polyethylene foam compressed to three different thicknesses.

TABLE 1

| Density (g/cm³) | | Thickness (mm) |
|---|---|---|
| Min | Max | |
| 0.07 | 0.09 | 4.5 |
| 0.22 | 0.28 | 1.5 |
| 0.33 | 0.43 | 1.0 |

EXAMPLES

Example 1

3 mm thick open celled polyurethane foam wound contact layer was compressed to 1.5 mm and adhesive bonded to 4 mm thick polyurethane foam absorbent layer using an acrylic pressure sensitive adhesive. The polyurethane foam absorbent layer was then adhesive bonded to a polyurethane 30 micron film. A 20% BP CHG solution was dosed onto the wound contact layer and the dressing was heat treated to leave approximately 92 mg of CHG within the wound contact layer.

Example 2

3 mm thick open celled polyurethane foam wound contact layer was compressed to 1.5 mm and adhesive bonded to 3.25 mm thick polyurethane foam absorbent layer using an acrylic pressure sensitive adhesive. The polyurethane foam absorbent layer was then adhesive bonded to a polyurethane 30 micron film. A 20% BP CHG solution was dosed onto the wound contact layer and the dressing was heat treated to leave approximately 92 mg of CHG within the wound contact layer.

Example 3

1.5 mm thick open celled polyurethane foam wound contact layer was adhesive bonded to 4 mm thick polyurethane foam absorbent layer using an acrylic pressure sensitive adhesive. The polyurethane foam absorbent layer was then adhesive bonded to a polyurethane 30 micron film. A 20% BP CHG solution was dosed onto the wound contact layer and the dressing was heat treated to leave approximately 92 mg of CHG within the wound contact layer.

Example 4

3 mm thick open celled polyurethane foam wound contact layer was compressed to 1.5 mm and adhesive bonded to 4 mm thick polyurethane foam containing approximately 0.13% Ag using an acrylic pressure sensitive adhesive. The polyurethane foam absorbent layer was then adhesive bonded to a polyurethane 30 micron film. A 20% BP CHG solution was dosed onto the wound contact layer and the dressing was heat treated to leave approximately 92 mg of CHG within the wound contact layer.

Example 5

3 mm thick open celled polyurethane foam wound contact layer was compressed to 1.5 mm and adhesive bonded to 4 mm thick polyurethane foam containing approximately 0.13% Ag using an acrylic pressure sensitive adhesive. The polyurethane foam absorbent layer was then adhesive bonded to a polyurethane 30 micron film. A 20% BP CHG solution was dosed onto the wound contact layer and the dressing was heat treated to leave approximately 50 mg of CHG within the wound contact layer.

Example 6

3 mm thick open celled polyurethane foam wound contact layer was compressed to 1.5 mm and adhesive bonded to 4 mm thick polyurethane foam absorbent layer using an acrylic pressure sensitive adhesive. The polyurethane foam absorbent layer was then adhesive bonded to a polyurethane 30 micron film. A chitosan lactate solution was dosed onto the wound contact layer and the dressing was heat treated to leave approximately 50 mg of chitosan lactate within the wound contact layer.

Example 7

3 mm thick open celled polyurethane foam wound contact layer was compressed to 1.5 mm and adhesive bonded to 2.5 mm thick polyurethane foam absorbent layer using an acrylic pressure sensitive adhesive. The polyurethane foam absorbent layer was then adhesive bonded to a polyacrylate superabsorbent nonwoven material with a net heat bonded on the side distal to the wound surface. The superabsorbent material was then adhesive bonded to a polyurethane 30 micron film. A chitosan lactate solution was dosed onto the wound contact layer and the dressing was heat treated to leave approximately 92 mg of chitosan lactate within the wound contact layer.

Example 8

3 mm thick open celled polyurethane foam wound contact layer was compressed to 1.5 mm and adhesive bonded to 3.25 mm thick polyurethane foam absorbent layer using an acrylic pressure sensitive adhesive. On a proximal side of the polyurethane foam wound contact layer was bonded a perforated silicone coated polyurethane film. The polyurethane foam absorbent layer was adhesive bonded to polyurethane 30 micron film. A 20% BP CHG solution was dosed onto the wound contact layer and the dressing was heat treated to leave approximately 92 mg of CHG within the wound contact layer.

Test Methods

Absorbency:

An area of a test wound dressing is cut to 50×50 mm size and weighed. The test wound dressing is then fully immersed in saline solution for 30 minutes. After 30 minutes, the test wound dressing is removed by a corner of the dressing and allowed to drain for 15 seconds. The test wound dressing is then re-weighed and the fluid increase based on g/g calculated.

Wicking Rate:

An area of a test wound dressing is cut to 50×50 mm size. 2 g of saline solution is measured and pipetted onto the surface of the test article. The time taken for the 2 g of saline solution to be absorbed into the test article is recorded.

Comparative Testing

The wound dressing of the present invention was tested in comparison to Biopatch®, an antimicrobial dressing currently available on the market. The results are explained below.

A wound dressing of the present invention was prepared according to Example 2.

The wound dressing of the present invention comprised a 25 mm diameter disc comprising a central 4 mm hole and radial slit extending from the central hole to the edge of the disc.

For comparison purposes, a Biopatch® disc was obtained having a diameter of 25 mm comprising a central 4 mm hole and radial slit extending from the central hole to the edge of the disc.

TABLE 2

| Absorbency: | |
| --- | --- |
| Example 2 test dressing | >10.0 g/g |
| Biopatch ® | >8.0 g/g |

TABLE 3

| Antimicrobial content: | |
| --- | --- |
| Example 2 test dressing | 87 +/− 2 mg |
| Biopatch ® | 89 +/− 2 mg |

Elution Test:

An elution test was method devised to assess the level of CHG eluted from the each test dressing. The higher the elution value, the more CHG is being delivered to the microorganisms at the wound interface and within the wound dressing, the theory being that the more antimicrobial agent that can be exposed to the microorganisms, the greater the kill rate.

The aim of the test method is to determine the elution profile from the CHG impregnated test materials.

The following test method was followed:
(1) bond test wound dressing to a 30 mm diameter disc of Corex, backing membrane side down, to prevent the test wound dressing from curling throughout testing;
(2) wet a filter paper disc with 0.4 ml of deionised water;
(3) place the test wound dressing onto the filter paper;
(4) place the test wound dressing/filter paper inside a foil pouch, ensuring that the filter paper remains in contact with the entire surface of the wound contact layer side of the wound dressing;
(5) seal the pouch using a vacuum, to maintain contact between the filter paper and surface of the wound dressing;
(6) store the wound dressings at ambient conditions;
(7) at the required time interval carefully open the pouch & remove the test wound dressing/filter paper;
(8) remove the filter paper from beneath the test wound dressing;
(9) submerge the filter paper in a set amount of deionised water;
(10) leave the filter paper submerged for 60 minutes;
(11) measure the conductivity reading of the solution;
(12) record the result;
(13) repeat steps 3-12, using the same test article, at further time intervals;
(14) calculate the amount of CHG (mg) from Conductivity ($\mu$S/cm) at the different time points.

Figure 5:
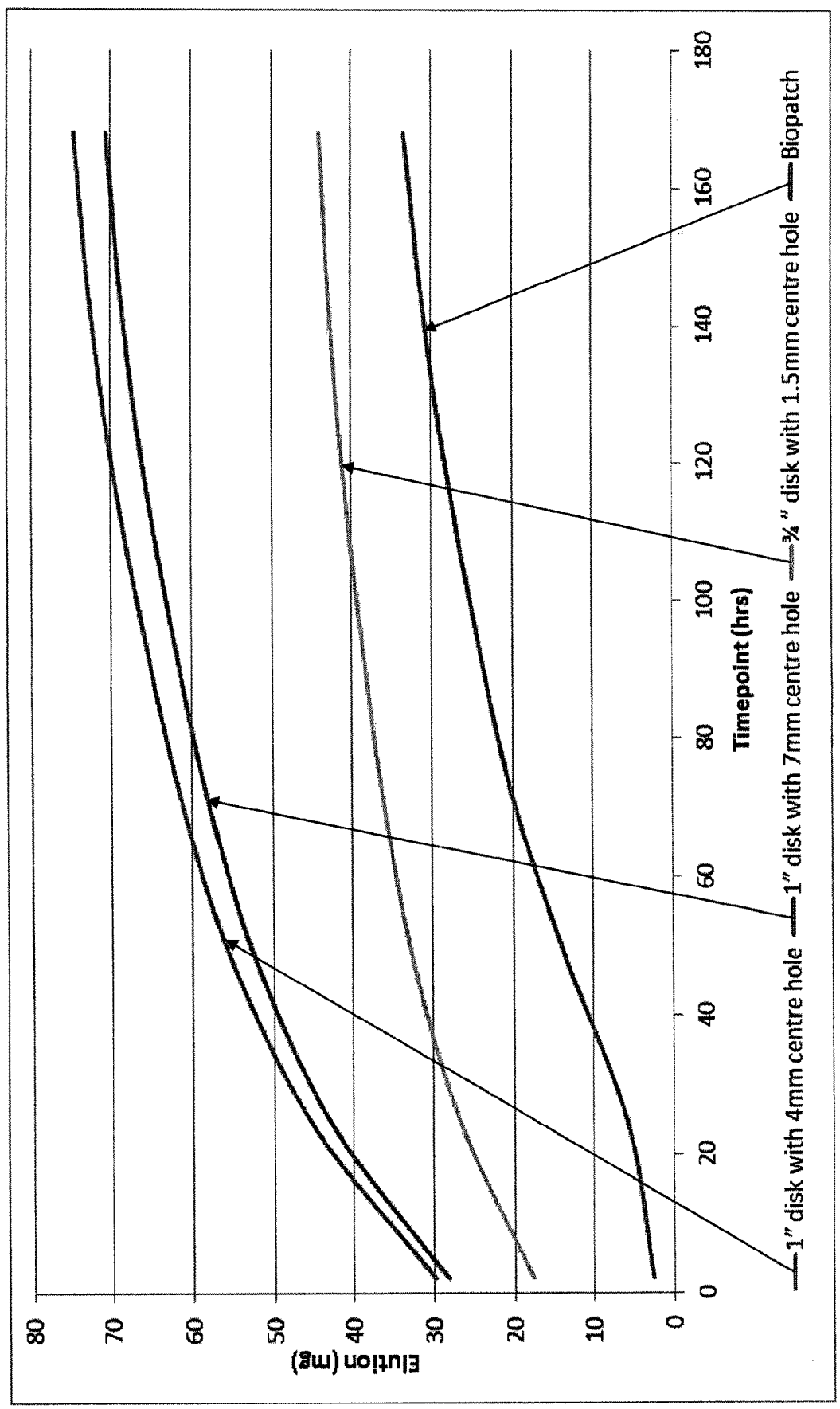
FIG. 5: is a graph showing the results of an elution test.

The results of the testing are shown in FIG. 5 and Table 4 below.

TABLE 4

| | Cumulative elution CHG (mg) over time | | | | | | | |
| --- | --- | --- | --- | --- | --- | --- | --- | --- |
| | Time Point (hrs) | | | | | | | |
| Sample Type | 2 | 24 | 48 | 72 | 96 | 120 | 144 | 168 |
| Example 2 test dressing | 29.82 | 45.05 | 55.16 | 61.58 | 66.13 | 69.94 | 72.72 | 74.67 |
| Example 2 test dressing with 7 mm centre hole | 28.20 | 42.60 | 52.16 | 58.23 | 62.54 | 66.14 | 68.77 | 70.61 |

TABLE 4-continued

Cumulative elution CHG (mg) over time

| Sample Type | Time Point (hrs) | | | | | | |
|---|---|---|---|---|---|---|---|
| | 2 | 24 | 48 | 72 | 96 | 120 | 144 | 168 |
| Composition as in Example 2 but as a 19 mm disc with 1.5 mm centre hole and radial slit | 17.57 | 26.54 | 32.49 | 36.27 | 38.95 | 41.20 | 42.84 | 43.98 |
| Biopatch ® | 2.55 | 5.67 | 13.31 | 20.15 | 24.63 | 28.33 | 31.19 | 33.44 |

It is clear from the Table 4 and from FIG. 5 that the Biopatch® dressing releases CHG at a far slower rate, around 10× slower, than the dressing of the present invention. As such, the dressing of the present invention is beneficial for application to wounds where a large quantity of antimicrobial agent needs to be delivered quickly.

It is of course to be understood that the present invention is not intended to be restricted to the foregoing examples which are described by way of example only.

The invention claimed is:

1. A wound dressing comprising a wound contact layer operable to absorb and laterally disperse wound exudate through the layer, the wound contact layer comprising a biologically acceptable polymer material selected from the group consisting of polyurethane foam, polyvinyl chloride foam, polyimide foam and silicone foam; and an absorption layer, the absorption layer being attached to the wound contact layer by an adhesive alone; wherein the wound contact layer comprises at least one antimicrobial agent and wherein the speed at which the wound contact layer absorbs wound exudate and allows it to disperse throughout the layer is higher than the speed at which the absorption layer absorbs wound exudate and allows it to disperse throughout the layer, and wherein the absorption layer comprises at least one antimicrobial agent and the concentration of the antimicrobial agent in the wound contact layer is higher than the concentration of the antimicrobial agent in the absorption layer.

2. A wound dressing as claimed in claim 1, wherein the absorbency of the wound contact layer is less than the absorbency of the absorption layer and/or wherein the absorbency of the wound contact layer is less than 20 g/g.

3. A wound dressing as claimed in claim 1, wherein the wound contact layer comprises polyurethane foam and/or wherein the thickness of the wound contact layer is from around 0.5 to 4 mm.

4. A wound dressing as claimed in claim 1, wherein the wound contact layer is compressed and/or wherein the wound contact layer has a density of greater than 0.06 g/cm$^3$, optionally wherein the wound contact layer is compressed to a width of from 20-90% of its original width.

5. A wound dressing as claimed in claim 1, wherein the antimicrobial agent is selected from the group consisting of silver, polyhexamethylene biguanide, chlorhexidine gluconate, chitosan, chitosan derivatives, octenidine, iodine and combinations of any two or more thereof.

6. A wound dressing as claimed in claim 1, wherein the absorption layer comprises an antimicrobial agent that is the same or different to the antimicrobial agent in the wound contact layer.

7. A wound dressing as claimed in claim 1, wherein the absorption layer swells by greater than 15% when fully saturated and/or wherein the absorption layer has a thickness of from 1 to 6 mm.

8. A wound dressing as claimed in claim 1, wherein the absorbency of the absorption layer is greater than 20 g/g; and/or wherein the absorption layer comprises polyurethane foam; and/or wherein the adhesive is acrylic based.

9. A wound dressing as claimed in claim 1, further comprising a backing layer, wherein the backing layer is optionally permeable to air and moisture but impermeable to water droplets and bacteria; and/or wherein the backing layer comprises a polyurethane film optionally having a thickness of from 10 to 100 microns.

10. A wound dressing as claimed in claim 1, further comprising a second absorption layer, wherein the second absorption layer optionally comprises a superabsorbent material; and/or further comprising a skin contact adhesive material attached to at least a portion of the wound contact layer, wherein the skin contact adhesive material optionally comprises an adhesive bonded to a carrier layer wherein the skin contact adhesive material optionally comprises a silicone adhesive bonded to a polyurethane film.

11. A wound dressing as claimed in claim 1, wherein the wound contact layer, when swelled and wet with wound exudate, does not expand outwardly but does expand vertically.

12. A wound dressing as claimed in claim 1, wherein the adhesive is in the form of a layer between the absorption layer and the wound contact layer and wherein the layer is porous so as to allow transmission of the wound exudate from the wound contact layer into the absorbent layer.

13. A wound dressing as claimed in claim 1, wherein the wound contact layer is in the form of an open cell foam and wherein the antimicrobial agent is applied in the form of a solution and is dispersed uniformly across and throughout the wound contact layer.

14. A wound dressing as claimed in claim 1, wherein the speed at which the wound contact layer absorbs wound exudate and allows it to disperse throughout the layer is uniform across the wound contact layer.

15. A wound dressing as claimed in claim 1, wherein the wound contact layer is an open cell foam.

16. A method of manufacturing a wound dressing, the method comprising the steps of:
  a. attaching a wound contact layer to an absorption layer using an adhesive alone, the wound contact layer comprising a biologically acceptable polymer material selected from the group consisting of polyurethane foam, polyvinyl chloride foam, polyimide foam and silicone foam; and
  b. applying at least one antimicrobial agent to the wound contact layer and the absorption layer;
wherein the speed at which the wound contact layer absorbs wound exudate and allows it to disperse throughout the layer is higher than the speed at which the absorption layer absorbs wound exudate and allows it to disperse throughout the layer and wherein the concentration of the antimicrobial agent in the wound contact layer is higher than the concentration of the antimicrobial agent in the absorption layer.

17. A method as claimed in claim 16, wherein the adhesive comprises an acrylic powder, wherein the powder is scattered onto a surface of the wound contact layer and/or the absorption layer and the wound contact layer and the absorption layer are then laminated; and/or wherein the antimicrobial agent is applied to the wound contact layer as a solution.

18. A method as claimed in claim 16, further comprising the step of drying the wound dressing; and/or attaching a backing layer to the absorption layer using an adhesive; and/or attaching an adhesion means to the wound contact layer, the adhesion means comprising an adhesive bonded to a carrier layer.

* * * * *